(12) United States Patent
Godwin et al.

(10) Patent No.: US 8,962,541 B2
(45) Date of Patent: Feb. 24, 2015

(54) PROCESSES RELATING TO ALCOHOLS FOR THE PRODUCTION OF ESTERS

(75) Inventors: Allen D. Godwin, Seabrook, TX (US);
Philippe L. Buess, Overijse (BE);
Raphael F. Caers, Edegem (BE); Arie Van Vliet, Sterrebeek (BE); Eddy T. A. Van Driessche, Eeklo (BE); Alfons Cuyckens, Erembodegem (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 550 days.

(21) Appl. No.: 13/139,949

(22) PCT Filed: Dec. 3, 2009

(86) PCT No.: PCT/EP2009/066289
§ 371 (c)(1),
(2), (4) Date: Sep. 7, 2011

(87) PCT Pub. No.: WO2010/079018
PCT Pub. Date: Jul. 15, 2010

(65) Prior Publication Data
US 2011/0312864 A1 Dec. 22, 2011

Related U.S. Application Data

(60) Provisional application No. 61/143,202, filed on Jan. 8, 2009.

(30) Foreign Application Priority Data

Feb. 20, 2009 (EP) .................................. 09153287

(51) Int. Cl.
| | | |
|---|---|---|
| *C10M 105/32* | (2006.01) |
| *C07C 31/125* | (2006.01) |
| *C07C 69/75* | (2006.01) |
| *C07C 69/78* | (2006.01) |
| *C08K 5/10* | (2006.01) |
| *C07C 29/141* | (2006.01) |
| *C07C 29/17* | (2006.01) |

(52) U.S. Cl.
CPC ........... *C07C 29/175* (2013.01); *C07C 2101/14* (2013.01); *C07C 29/141* (2013.01); *C08K 5/10* (2013.01)
USPC ........... 508/463; 508/496; 508/583; 524/287; 524/296; 524/298; 524/314; 524/315; 560/64; 560/103; 560/126; 560/180; 568/840

(58) Field of Classification Search
USPC .......................................... 508/583; 568/840
See application file for complete search history.

(56) References Cited

U.S. PATENT DOCUMENTS

| 3,232,848 A | 2/1966 | Johnson | |
|---|---|---|---|
| 3,239,566 A * | 3/1966 | Slaugh et al. | ................. 568/454 |

(Continued)

FOREIGN PATENT DOCUMENTS

| DE | 1 003 702 | 3/1957 |
|---|---|---|
| DE | 11 48 221 | 5/1963 |

(Continued)

*Primary Examiner* — Ellen McAvoy
(74) *Attorney, Agent, or Firm* — Luke A. Parsons; Leandro Arechederra, III (57) ABSTRACT

The present invention relates to alcohols and in particular to $C_4$ to $C_{15}$ alcohols that are used in the production of esters.

7 Claims, 4 Drawing Sheets

(56) References Cited

U.S. PATENT DOCUMENTS

| | | | |
|---|---|---|---|
| 3,491,158 A | 1/1970 | Reich | |
| 4,518,809 A * | 5/1985 | Forster et al. | 568/840 |
| 4,598,162 A * | 7/1986 | Forster et al. | 568/448 |
| 5,189,105 A * | 2/1993 | Miyazawa et al. | 252/182.12 |
| 5,468,419 A * | 11/1995 | Miyazawa et al. | 252/182.12 |
| 5,583,250 A * | 12/1996 | Bahrmann et al. | 560/76 |
| 7,227,045 B2 | 6/2007 | Ansorge et al. | 568/451 |
| 7,329,783 B2 * | 2/2008 | Mul | 568/451 |
| 7,335,802 B2 * | 2/2008 | Ayoub et al. | 568/909 |
| 7,667,080 B2 * | 2/2010 | Caers et al. | 568/840 |
| 7,781,620 B2 * | 8/2010 | Mul | 568/451 |
| 8,017,810 B2 * | 9/2011 | Mul | 568/454 |
| 8,017,811 B2 * | 9/2011 | Mul | 568/454 |
| 8,044,249 B2 * | 10/2011 | Scheibel et al. | 568/853 |
| 8,049,043 B2 * | 11/2011 | Caers et al. | 568/454 |
| 8,232,432 B2 * | 7/2012 | Scheibel et al. | 568/853 |
| 8,299,308 B2 * | 10/2012 | Scheibel et al. | 568/494 |
| 2006/0105465 A1 | 5/2006 | Weber et al. | |
| 2008/0242899 A1 | 10/2008 | Oota et al. | |

FOREIGN PATENT DOCUMENTS

| | | |
|---|---|---|
| EP | 0343819 | 11/1989 |
| EP | 1 669 337 | 6/2006 |
| GB | 923 464 | 4/1963 |
| GB | 1 249 133 | 10/1971 |
| GB | 1 252 678 | 11/1971 |
| GB | 1 336 776 | 11/1973 |

* cited by examiner

PROCESSES RELATING TO ALCOHOLS FOR THE PRODUCTION OF ESTERS

CROSS-REFERENCE TO RELATED APPLICATIONS

This application is a 371 National Stage Application of International Application No. PCT/EP2009/066289, filed Dec. 3, 2009, which claims the benefit of Ser. No. 61/143,202, filed Jan. 8, 2009, the disclosures of which are incorporated herein by reference in their entireties.

FIELD OF THE INVENTION

The present invention relates to alcohols and in particular to $C_4$ to $C_{15}$ alcohols that are used in the production of esters. The invention further relates to esters derived from these alcohols, and to the use of such esters as plasticiser or lubricant esters. The higher carbon number alcohols of the invention may also be used in surfactant derivatives like ethoxylates, sulfates, or ethoxysulfates.

The present invention also relates to a process for producing the alcohols. The invention also relates to higher olefins, in particular to $C_5$ to $C_{14}$ olefins, which are useful as starting materials in the production of the alcohols of the present invention.

BACKGROUND OF THE INVENTION

Many end uses of esters made from alcohols require the esters to have a low colour, preferably to be water white in colour. Many esters are intensively used as plasticisers for polyvinyl chloride (PVC). Acetate esters are often used as solvents or as fragrance components. Acrylate or methacrylate esters are used as such or as their polymers in the production of coatings, paints, adhesives, in the caulking of building materials, or as binders for leather, paper or textiles. Plasticisers, solvents and fragrance components should have a low colour, and should also have an acceptable odour. Plasticisers should also be resistant to ultra violet light as they are often used in articles exposed to sunlight. The plasticiser should contain only a minimal amount of volatile components or light ends so that it has a low odour level both during its processing and in its final application.

Plasticiser and lubricant esters are typically made by esterification of $C_6$ to $C_{15}$ alcohols with an acid or anhydride, such as the various isomers of phthalic acid, primarily (ortho-) phthalic anhydride, cyclohexane mono- or dicarboxylic acids or anhydrides, adipic acid, trimellitic acid and its anhydride, or the various isomers of pyromellitic acid or their anhydrides. Acetate, acrylate or methacrylate esters are typically made with $C_4$ to $C_{10}$ alcohols. The alcohols themselves are in many instances made by employing hydroformylation of olefins; such alcohols are also known as oxo alcohols. Oxo alcohols are primary alcohols and typically have branched alkyl chains. Occasionally they comprise, or are primarily, straight chain primary alcohols. In such case they are made from linear alpha olefins (LAOs), which typically have an even carbon number. The alcohols derived from even carbon numbered LAOs by hydroformylation (which adds a carbon atom to the LAOs) have an odd number of carbon atoms per molecule. Normal or nearly-normal alcohols with even carbon numbers may also be made by hydroformylation.

There are two main synthetic processes for the production of oxo alcohols. One process involves hydroformylation and hydrogenation, possibly preceded by olefin oligomerisation to produce an olefin having a higher carbon number, often referred to as a higher olefin, as the hydroformylation feed. Another main process involves olefin hydroformylation followed by aldol condensation and hydrogenation. The starting materials for all these processes are olefins which may be single olefins or, more commonly, mixtures of olefins. The oligomerisation, hydroformylation, hydrogenation and condensation reactions are all catalysed and tend to involve several different reactions. Accordingly, in many of the steps of both processes, complex reaction mixtures tend to be formed. The final alcohol therefore requires extensive purification to remove unreacted raw materials, undesirable byproducts and catalyst residues. Purification typically involves washing, further hydrogenation or hydrofinishing, and fractional distillation. However, despite rigorous purification, the purified oxo-alcohols invariably contain small amounts of impurities.

Esters are produced by reaction of the appropriate alcohol with an acid or anhydride. In the production of plasticiser ester, the most commonly used anhydrides are phthalic anhydride, trimellitic anhydride, or maleic anhydride. Frequently used acids include adipic acid, trimellitic acid, cyclohexanoic mono- and dibasic acids, benzoic acid, citric acid and the like. Acetates are produced by reaction of the alcohol with acetic acid or its anhydride. Acrylates and methacrylates are typically produced by reaction with acrylic or methacrylic acid.

Alcohol esterification is typically also a catalysed reaction, in many instances an acid catalysed reaction. Examples of acid catalysts include Brönsted acids such as sulfuric acid, methane sulfonic acid and paratoluene sulfonic acid, and Lewis acids such as tin and titanium based organometallic catalysts. Heat is typically provided to the esterification reaction, and it has been found that higher esterification temperatures improve the efficiency of the esterification process.

It is important that the alcohol is stable under the modern esterification conditions, which have become more severe than in the past. One problem with alcohols is that they can develop an undesirable colour under esterification conditions, thus leading to an undesirable colour in the ester formed, which, accordingly, is either not useful, or requires further treatment to reduce the colour back to an acceptable level. We have now found that colour development may occur during esterification using acid catalysts, if small amounts of conjugated unsaturated carbonyl containing compounds are present in the alcohol. By conjugated we mean that the compounds contain ethylenic unsaturation that is conjugated with a carbonyl group in the same molecule. We have also found that conjugated unsaturated aldehydes are greater colour generators than conjugated unsaturated ketones.

Without wishing to be bound by any theory, we believe that the presence of the conjugated unsaturated carbonyl compounds in the alcohol may result from the production of these compounds by virtue of side reactions, particularly dehydration, during one of the steps of the alcohol production process, such as for example an oligomerisation step to produce a higher olefin, the hydroformylation step, the aldol condensation of two aldehydes, or the hydrogenation step. We have also found that these compounds may also result from the presence of impurities in the olefin feeds that are used in the oligomerisation or in the hydroformylation reaction; for example, dienes present in the feed may be hydrated and then dehydrogenated. Surprisingly, some of the conjugated unsaturated carbonyl compounds present in the olefin feeds to hydroformylation appear to be unaffected by the typical distillation and hydrogenation techniques used in commercial alcohol manufacture, and we have found that significant amounts remain in existence through hydroformylation and hydrogenation. They can therefore be present in the alcohol, and in sufficient quantities to have an adverse effect on colour when the alcohol is subjected to acid conditions. We have also found that although both ketones and aldehydes can be formed, they may be formed in oligomerisation coincidentally more ketones than aldehydes.

U.S. Pat. No. 3,232,848 relates to a method of refining synthetically produced alcohols, and to a method of improving the colour quality of synthetic alcohols and their chemical derivatives. U.S. Pat. No. 3,232,848 states that the impurities present in synthetic alcohols are extremely complex in nature and are generally thought to be contaminating amounts of aldehydic and unsaturated compounds, which are introduced into the alcohol by its method of manufacture. The test used for colour in U.S. Pat. No. 3,232,848 is similar to the sulphuric acid test ASTM D 1209-54 which has been superseded a.o. by ASTM E 852-94a, a test which is discussed in more detail, later on in this document. U.S. Pat. No. 3,232,848 suggests that an alcohol of improved colour quality may be provided by a post treatment of the alcohol involving stripping and distillation in the presence of a phosphorous-containing acid.

United Kingdom Patent No. 1336776 is concerned with the production of colourless esters using strong acid catalysts, and states that the presence of trace amounts of carbonyl and ethylenic groups in the alcohols used in the production of the esters results in colouring the esters. The esterification reaction runs for 3 hrs at 135° C. It is stated that the impurities can also develop during esterification, and this document suggests that the problem may be overcome by conducting the esterification reaction in a hydrogenating medium in the presence of a hydrogenation catalyst so that hydrogenation conditions prevail throughout the esterification reaction.

United Kingdom Patent No. 923464 is concerned with the purification of alcohols produced by the Ziegler process, which is an ethylene growth process using aluminium alkyls. It is stated that the presence of contaminants such as aldehydes, esters and aldol-condensation products are capable of imparting colour to alcohols.

United States Patent publication No. 2006/0105465 discloses a colorimetric technique for quantitative analysis of carbonyl functions, i.e. aldehydes and/or ketones in a sample comprising synthetic $C_4$-$C_{15}$ alcohols obtained by the Oxo process. The technique comprises the reaction of the carbonyl function with 2,4-dinitrophenylhydrazine with an acid to form a hydrazone, which is very fast in the presence of sulphuric acid. Subsequently, the hydrazone may be reacted with potassium hydroxide to form a coloured species, the concentration of which may then be determined by spectrophotometry, preferably using the yellowness colour index according to ASTM E-313. The result is obtainable in a matter of minutes, and therefore, also suitable for application in the field. The technique is shown to analyse for all carbonyl functions, without differentiation. US 2006/0105465 discloses a series of alcohols produced by the Oxo process for which the carbonyl number was determined.

DE 1148221 and related U.S. Pat. No. 3,373,211 are concerned with the presence of carbonyl compounds, saturated or unsaturated, in oxo alcohols and in alcohols prepared by the oxidation and subsequent hydrolysis of aluminum alkyls, and their effect on the colour of the phthalate ester derivative. These documents disclose that such $C_6$ to $C_{16}$ alcohols, even after extensive fractionation, contain generally from 0.01 to 1.0 wt. percent of carbonyl compounds. A concentration of 0.01 wt % $C_6$ carbonyl compound is equivalent to a carbonyl presence of 1 meq/kg and with a carbonyl number of 0.056 mg KOH/g. A crude stripped decyl alcohol stream, prior to final fractionation and thus containing high molecular weight dimer and trimer product sometimes referred to as oxo bottoms, is disclosed to contain a level of 0.02 wt % carbonyl compounds. The documents do not disclose to what level these carbonyls are concentrated up during the final fractionation, or how much extra carbonyls, saturated or unsaturated, may be formed during such final fractionation, for instance because of oxygen ingress causing oxidative dehydrogenation in the vacuum tower, the entrainment of hydrogenation catalyst fines or of other trace compounds causing side reactions such as the Guerbet alcohol condensation reaction, which mechanism is believed to pass via unsaturated intermediates. The purity requirements for such alcohols have evolved since the 1960's and have nowadays become much more stringent. The same may be said with respect to the disclosure in GB 1252678.

So far, the cause for colour formation in Hot Sulphuric Acid colour tests, such as ASTM E 852-94a or ASTM D5398, has not been clearly identified. The Hot Sulphuric Acid Colour formation may be indicative for the presence of aldehydes, which, in the test, may aldolise and dehydrate to form colour forming bodies. We have also found that the presence of aldehydes in larger amounts may lead to a stronger colour result in the Hot Sulphuric Acid Colour test. Therefore, alcohols intended for esterification should not contain more than a certain level of carbonyl functions, as measured by a known carbonyl test, such as the test described in US 2006/0105465, the disclosure of which is herewith enclosed by reference. Commercial alcohols are therefore typically offered with a maximum carbonyl number as a product specification. Occasionally, a maximum colour reading on the Pt/Co scale according to the Hot Sulphuric Acid Colour test is also specified. It is however not clear which contaminants are relevant for such a specification on the alcohol, nor which levels thereof would be unacceptable. The Hot Sulphuric Acid Colour test therefore is a convenient and indicative tool, but conclusions that may be drawn from its outcome are limited, in particular quantitative conclusions. Therefore, in the production of alcohols, there remains a need for a sensitive and specific measurement method for conjugated unsaturated carbonyl functions, a technique which preferably would be suitable for use in an industrial environment, preferably in the field, such as an at-line or on-line analytical method. Such a method may also be complemented by a convenient carbonyl test for measuring total carbonyls, preferably also as an at-line or even on-line analytical method. Both methods together would then allow for a much closer quality monitoring of alcohol production processes, primarily of the hydrogenation steps in such processes, offering benefits of lower operating temperatures and pressures, longer catalyst lives, lower hydrogen requirements, and less offgasses and spent catalysts to be disposed of They also offer the capability to produce alcohols that are low in unsaturated conjugated carbonyl compounds.

In the present context, an at-line method means an analytical method that is executed by an operator in a field lab, located close to the location where the sample is taken. The sample is typically collected manually by the operator. The analytical method itself may or may not be automated. The advantage is that the result of the analysis is immediately available to the operator. An on-line analytical method is a method that takes its sample on-line, i.e. it is typically fully automated and operates without the intervention of an operator. The analytical procedure of an on-line method is usually also fully automated, so that no human intervention is usually required to generate the result. The result of an on-line analytical method is usually also communicated automatically, such as by electronic means, to more remote observers such as to a panel operator in a centralised control room.

The present invention is concerned with alcohol compositions that contain low levels of conjugated unsaturated carbonyl compounds. The undesirable conjugated unsaturated carbonyl compounds, with which the present invention is concerned, may be present in the alcohol for a variety of reasons. For example, depending upon the nature and origin of the olefin feed to hydroformylation, they may be present in the olefin feed or be developed during processing of the olefin feed. For instance $C_8$ olefins for the production of $C_9$ alcohols can be made by the dimerisation of butenes. Alternatively, butene feeds can be hydroformylated to produce $C_5$ aldehydes which are subject to an aldol reaction and hydrogenated to produce $C_{10}$ alcohols. Both reactions therefore use butene feeds. Feeds of petroleum origin are often used as the source of butene and these feeds can contain small amounts of butadiene. Furthermore small amounts of butadiene can be produced by dehydrogenation and isomerisation side reactions that can occur during the dimerisation reaction and the hydroformylation reaction, possibly by hydration and further dehydrogenation, and/or combined with hydrogen transfer. The butadiene may therefore be present, and be the precursor of unsaturated carbonyl compounds, some of which may be conjugated. Similarly, small amounts of other dienes may be present in other olefinic feeds and/or be produced during the oligomerisation thereof to produce olefinic feeds for hydroformylation. Conjugated unsaturated carbonyl compounds may also be produced in the hydroformylation reaction, for instance by dehydration of a hydroxy or dihydroxy aldehyde, which may be produced by aldol condensation.

SUMMARY OF THE INVENTION

We have found that UV spectrophotometry is highly suitable for monitoring the quality of alcohol and of the alcohol production processes, in particular for determining the amount of unsaturated conjugated carbonyl compounds in the alcohol product and in other process streams, and this, down to very low levels. The present invention therefore provides for the use of a UV spectrophotometry analytical method for monitoring alcohol quality in association with an alcohol production process or an alcohol consumption process.

We have found that the UV spectrophotometry method according to the current invention is capable of determining concentrations of conjugated unsaturated carbonyl compounds in samples containing alcohols and other oxygenates down to a level of 0.02 meq/kg, which is a concentration that would contribute only about 0.001 mg KOH/g to a carbonyl number measured on the same sample. The UV spectrophotometry method of the present invention, when properly calibrated for a particular process and process stream, is simple to use and gives a fast response, making it very suitable for application in the field, such as at-line or even on-line.

We have also found that, in addition, this monitoring may be further improved by using the carbonyl determination method, which is suitable for at-line or even on-line measurement, as disclosed in US 2006/0105465. The present invention therefore provides for the use of this carbonyl determination method in combination with the UV spectrophotometry method, described in detail herewith.

In another embodiment, the present invention provides for a process for the production of alcohols, whereby the hydrogenation reaction is monitored by the UV spectrophotometry test of the present invention, preferably in combination with the aforementioned carbonyl determination method.

We have found that alcohols that are substantially free of conjugated unsaturated carbonyl compounds, particularly conjugated unsaturated aldehydes, produce esters having a reduced colour, especially when they are produced by an esterification process using an acid catalyst, especially a Brönsted acid catalyst. We have also found that when such alcohols are subjected to the Hot Sulphuric Acid Colour test, they have a reduced tendency to form colour. Further cleanup of the esterification product may therefore be simplified, consume less chemicals and/or utilities and generate lower volumes of discard material such as waste adsorbents. When used in esterification processes, such alcohols lead to esters having a lower colour.

We have also found that, if olefinic feeds to the hydroformylation reaction used in the production of alcohols are substantially free of conjugated unsaturated carbonyl compounds, particularly conjugated unsaturated aldehydes, the alcohols produced from these olefinic feeds by hydroformylation reaction have a reduced tendency to form colour when subjected to the Hot Sulphuric Acid Colour test, and bring the same associated advantages as explained hereinbefore.

The present invention therefore also provides a $C_4$ to $C_{15}$ alcohol composition containing at most 1.78 meq/kg of conjugated unsaturated carbonyl compounds, whereby,
(i) if the nominal average carbon number of the alcohol mixture is 6, the mixture contains at most 0.99 meq/kg of conjugated unsaturated carbonyl compounds,
(ii) if the nominal average carbon number of the alcohol mixture is 7 or 8, the mixture contains at most 0.17 meq/kg of conjugated unsaturated carbonyl compounds,
(iii) if the nominal average carbon number of the alcohol mixture is 9 or 13, the mixture contains at most 0.88 meq/kg of conjugated unsaturated carbonyl compounds, and
(iv) if the nominal average carbon number of the alcohol mixture is 10, the mixture contains at most 1.05 meq/kg of conjugated unsaturated carbonyl compounds.

The conjugated unsaturated carbonyl compounds may comprise at least one conjugated unsaturated aldehyde. Aldehydes may represent the majority or all of the conjugated unsaturated carbonyl compounds.

The present invention further provides a $C_5$ to $C_{14}$ olefin, useful in the production of a $C_6$ to $C_{15}$ alcohol, and containing at most 13.5 meq/kg of conjugated unsaturated carbonyl compounds.

The conjugated unsaturated carbonyl compounds in the olefins of the present invention may be conjugated unsaturated aldehydes and/or conjugated unsaturated ketones.

The present invention further provides a process for the production of a $C_4$ to $C_{15}$ oxo-alcohol comprising a hydroformylation step, a hydrogenation step and a step for distilling the product alcohol from the hydrogenation product, selected from
(a) hydroformylating in the hydroformylation step a $C_3$ to $C_{14}$ olefin and hydrogenating in the hydrogenation step the product of hydroformylation to form the $C_4$ to $C_{15}$ oxo-alcohol, and
(b) hydroformylating in the hydroformylation step a $C_2$ to $C_4$ olefin to form a $C_3$ to $C_5$ aldehyde, aldolising the $C_3$ to $C_5$ aldehyde in at least one aldol step to a dimer, trimer or tetramer thereof which is a branched $C_6$ to $C_{15}$ aldehyde, and hydrogenating in the hydrogenation step the branched $C_6$ to $C_{15}$ aldehyde to a branched $C_6$ to $C_{15}$ alcohol,
whereby the content of conjugated unsaturated carbonyl compounds in the $C_4$ to $C_{15}$ alcohol is reduced by at least one of the steps selected from
(i) if the olefin feed to the hydroformylation step in (a) is a $C_6$ to $C_{14}$ olefin, treating the $C_6$ to $C_{14}$ olefin feed to hydroformylation in (a) to reduce its content of conjugated unsaturated carbonyl compounds to below 13.5 meq/kg, (ii) treating the product of the hydrogenation step in (a) or (b) to reduce its content of conjugated unsaturated carbonyl compounds to below 13.5 meq/kg, and
(iii) treating the product alcohol from the distillation step of the process to reduce its content of conjugated unsaturated carbonyl compounds to below 1.78 meq/kg.

The invention further provides for an ester derived from the alcohol of the present invention. The ester has a lower colour, which is an advantage in many end-uses for the esters of the present invention.

The invention further provides for the use of the ester of the present invention as a plasticiser for polyvinyl chloride, and as a synthetic lubricant.

DETAILED DESCRIPTION

The alcohol composition of the invention may be straight chain or branched. The alcohol composition of the invention may be a mixture of alcohols. The mixture may contain alcohols having different carbon numbers and/or different alkyl groups. The mixture may contain branched alcohols and/or normal or straight chain alcohols, which may also be called linear alcohols. The alcohol composition according to the invention is preferably an oxo alcohol composition or a Ziegler alcohol composition. It has been discussed hereinabove that the processes leading to these alcohols, in particular the hydroformylation step and the aldolisation step, but even any distillation steps, are known to introduce conjugated unsaturated carbonyl compounds, and that these compounds are usually not removed by the conventional purification techniques down to the desired very low levels required for the production of high quality alcohol derivatives.

The alcohol of the invention may contain any number of carbon atoms in its molecule that is in the range from 4 to 15, preferably 5, 6, 7, 8, 9, 10, 11, 12, 13 or 14. When the alcohol comprises a mixture of alcohols, the mixture may comprise alcohols having different carbon numbers. A portion of the alcohols in the alcohol mixture may then have a carbon number that is outside the specified range, provided that the average carbon number is in the specified range. The average carbon number of an alcohol mixture is preferably rounded to the nearest integer, which result then is called the nominal average carbon number of the alcohol or alcohol mixture. The nominal average carbon number of the alcohol of the present invention is then in the specified range.

The carbon number distribution of alcohols according to the present invention may be readily determined by methods known in the art. For example, we have found that a boiling point gas chromatography (GC) method, calibrated with the suitable consecutive series of straight chain alcohols, is suitable for this purpose. In such a method, the GC spectrum is typically split into the individual carbon numbers by allocating the GC peaks that elute at a retention time in between the retention times of two consecutive straight chain alcohols, the number of carbons of the highest of the two delimiting straight chain alcohols.

The alcohol of the present invention contains at most 1.78 meq/kg of conjugated unsaturated carbonyl compounds. Preferably the alcohol contains at most 1.50 meq/kg, more preferably at most 1.20 meq/kg, even more preferably at most 1.05 meq/kg, yet more preferably at most 0.99 meq/kg, even more preferably at most 0.98 meq/kg or 0.95 meq/kg, yet more preferably at most 0.88 meq/kg, again more preferably at most 0.50 meq/kg, still more preferably at most 0.41 meq/kg, yet more preferably at most 0.35 meq/kg or even 0.20 meq/kg, and even more preferably at most 0.17 meq/kg of conjugated unsaturated carbonyl compounds. Most preferably the alcohol contains at most 0.087 meq/kg of conjugated unsaturated carbonyl compounds, in particular if the nominal average carbon number of the alcohol is 8. If the nominal average carbon number of the alcohol is 10, we most prefer that the alcohol of the present invention contains at most 0.71 meq/kg of conjugated unsaturated carbonyl compounds.

The branched alcohol of the present invention may be a single isomer alcohol. Suitable examples are 2-ethyl hexanol obtainable from propylene, 2,4-dimethyl heptanol obtainable from ethylene, and 2-propyl heptanol obtainable from n-butenes or 1-butene, employing a combination of hydroformylation, aldolisation and hydrogenation steps known in the art. The alcohol of the present invention may have one, two, three or four branches per molecule. We prefer the alcohol to have only three, preferably only two and more preferably only one branch per molecule. An alcohol having fewer branches per molecule allows the production of ester derivatives having a lower viscosity. In case of a phthalate or an adipate ester used as plasticiser for polyvinyl chloride (PVC), the PVC plastisol made with the lower viscosity ester will also have a lower viscosity and be easier to process, particularly in a plastisol application.

The branched alcohol of the present invention may be a mixture of alcohols having different branched alkyl chains. The number of branches per molecule may be the same for all of the alcohols in the mixture. The alcohol may also be a mixture of alcohols having a different number of branches per molecule, in which case an average number of branches per molecule may be determined. We prefer to use $^1$H-NMR to determine the average branchiness. This technique, and how it may lead to an average branchiness of an alcohol, is described in detail in WO 2006/012989 for isononyl alcohols; we have found that this method is also suitable for other carbon numbers. We prefer the alcohol of the present invention to have an average branchiness per molecule that is in the range of from 0.1 to 4.0, preferably from 0.3 to 3.1, more preferably from 0.35 to 2.7, even more preferably from 0.4 to 2.2, yet more preferably from 0.45 to 2.1, even more preferably from 0.5 to 1.5 and most preferably from 0.55 to 1.2.

The branched alcohols of the present invention may have only one branch, and this branch may always be on the second carbon position relative to the OH-function of the alcohol. Suitable alcohols may be 2-ethyl hexanol and 2-propyl heptanol. Branched alcohols may also be made from other lower molecular weight alcohols using the Guerbet reaction, in which two alcohol molecules condense to a dimer primary alcohol molecule that has a branch on the second carbon position relative to the OH-function. When the starting alcohols of the Guerbet reaction are straight chain alcohols, the derived Guerbet alcohol will only have one branch, and 100% of the branches will be on the second carbon position relative to the alcohol or OH-function.

The branched alcohol of the present invention may be a mixture of alcohol molecules having different structures. In one embodiment of the current invention, at most 90% by mole of the alcohol molecules have their first branch on the second carbon position relative to the alcohol or OH-function. Suitable alcohols are the oxo-alcohols obtainable via the hydroformylation of higher olefins. The portion of the alcohol molecules having their first branch on the second carbon position relative to the alcohol or OH-function may be determined by techniques known in the art. For example, a $^{13}$C-NMR method may be used, as also described in detail in WO 2006/012989, a disclosure that is herewith fully incorporated by reference.

The present invention also provides for an olefin that is useful in the production of the alcohol of the present invention, and which is a $C_5$ to $C_{14}$ olefin containing at most 13.5 meq/kg of conjugated unsaturated carbonyl compounds. The olefin may be a higher olefin. We prefer the olefin to contain at most 12.5 meq/kg, preferably at most 10 meq/kg, more preferably at most 8 meq/kg, even more preferably at most 5.0 meq/kg, yet more preferably at most 3.00 meq/kg, again more preferably at most 2.00 meq/kg conjugated unsaturated carbonyl compounds.

The olefin of the present invention may contain also lower amounts of conjugated unsaturated carbonyl compounds, such as at most 1.78 meq/kg, preferably at most 1.50 meq/kg, more preferably at most 1.20 meq/kg, even more preferably at most 1.05 meq/kg, yet more preferably at most 0.88 meq/kg, again more preferably at most 0.50 meq/kg, still more preferably at most 0.35 meq/kg or even 0.20 meq/kg and even more preferably at most 0.17 meq/kg of conjugated unsaturated carbonyl compounds. Most preferably the higher olefin of the present invention contains at most 0.087 meq/kg of conjugated unsaturated carbonyl compounds. The conjugated unsaturated carbonyl compounds may be conjugated unsaturated aldehydes, or they may be conjugated unsaturated ketones. The lower the level of conjugated unsaturated carbonyl compounds present in the olefin of the present invention, the lower the amount of such compounds that needs to be removed.

The olefin of the present invention may contain also higher amounts of conjugated unsaturated carbonyl compounds, such as at most 50 meq/kg, preferably at most 30 meq/kg, more preferably at most 20 meq/kg, even more preferably at most 15 meq/kg of conjugated unsaturated carbonyl compounds.

Preferably, the olefin of the invention is primarily branched. In one embodiment, the olefin is a mixture of olefins, preferably containing at least one branched olefin, but possibly also containing linear or unbranched olefins.

The olefin of the invention may contain any number of carbon atoms in its molecule that is in the range from 5 to 14, preferably 6, 7, 8, 9, 10, 11, 12 or 13. When the olefin comprises a mixture of olefins, the mixture may comprise olefins having different carbon numbers. A portion of the olefins in the olefin mixture may then have a carbon number that is outside the specified range, provided that the average carbon number is in the specified range. The average carbon number of an olefin mixture is preferably rounded to the nearest integer, which result then is called the nominal average carbon number of the olefin or olefin mixture. The nominal average carbon number of the olefin of the present invention is then in the specified range.

The carbon number composition of an olefin of the present invention may be readily determined by methods known in the art. For example, a boiling point hydrogenation gas chromatography (hydro-GC) method, calibrated with the suitable consecutive series of straight chain paraffins, is suitable for this purpose. In such a method, the olefins are hydrogenated to alcohols before entering the GC column, and the GC spectrum is typically split into the individual carbon numbers by allocating a carbon number to each of the GC peaks eluting at a certain retention time relative to the two retention times of two consecutive straight chain paraffins appearing before and after the retention time of interest. The number of carbons of the highest of the two delimiting straight chain paraffins is then attributed to the peak being determined.

Preferably, the olefin of the invention comprises a mixture of olefins having a nominal average carbon number in the range of from 6 to 12, preferably from 7 to 11, more preferably from 8 to 10, and even more preferably 9. A highly preferred olefin of the invention is an octene mixture obtained from butene dimerisation.

The branched olefin of the present invention may be a mixture of olefins having structures with different branchiness. The number of branches per molecule may be the same for all of the olefins in the mixture. The olefin may also be a mixture of olefins having different numbers of branches per molecule, in which case an average number of branches per molecule may be determined. For many of the lighter olefin mixtures, typically up to and including nonene mixtures, the individual isomer peaks in a boiling point GC, or a hydro-GC, may be identified, and an average branchiness may be determined from the GC-spectrum or from the hydro-GC spectrum. Also $^1$H-NMR may be used to determine the average branchiness of olefin mixtures, provided the average carbon number is known, including those containing more than 9 carbon numbers. Preferably the olefin of the present invention has an average branchiness per molecule that is in the range of from 0.1 to 4.0, preferably from 0.3 to 3.1, more preferably from 0.35 to 2.7, even more preferably from 0.4 to 2.2, yet more preferably from 0.45 to 2.1, even more preferably from 0.5 to 1.5 and most preferably from 0.55 to 1.2.

For example, suitable olefins may be mixtures of $C_5$ to $C_{12}$ olefins obtained by the phosphoric acid or zeolite catalysed oligomerisation of mainly $C_3$ and $C_4$ olefins and mixtures thereof. $C_5$ olefins may also be present during oligomerisation, as well as traces of ethylene. Where olefin mixtures are used as feed for hydroformylation, they may have been fractionated to obtain relatively narrow boiling cut mixtures of mostly the appropriate carbon number for the production of aldehydes and alcohols with the desired carbon number. Alternatively the olefins may be obtained by other oligomerisation techniques. Such techniques include the dimerisation or trimerisation of butene using a nickel-based or nickel oxide catalyst, like the Octol® process or the process described in U.S. Pat. No. 6,437,170. Others include oligomerisation processes for ethylene, propylene, pentenes and/or butenes, preferably single carbon number feedstocks and more preferably the unbranched, even more preferably terminal olefins such as butene-1, using a nickel salt and involving di-alkyl aluminium halides, like the range of Dimersol® processes. Yet other processes employ a zeolite or a molecular sieve oligomerisation catalyst for the oligomerisation of propylene and/or butenes and/or pentenes. The olefin products of these processes are typically branched and contain relatively low amounts of linear olefin isomers, typically less than 10 wt %.

The olefins may also be obtained from ethylene growth processes, such as the SHOP or the Ziegler processes, in which case they are often straight chain, preferably terminal olefins, and are called linear alpha olefins or normal alpha olefins. The SHOP process may include a metathesis step, in which case also uneven carbon numbers may be produced. The olefins from ethylene growth may have 6, 8, 10 or 12, or even higher carbon numbers such as up to 14, 16, 18 or even 20. The olefins may also be mixtures obtained from the Fischer-Tropsch process for the conversion of synthesis gas to hydrocarbons, which generates olefins of a range of carbon numbers, primarily containing terminal olefins but which may show some side branches along their longest alkyl chain, and which may also contain some internal olefins, linear and branched. In this case, also the higher carbon numbers may be useful starting liquids. Fischer-Tropsch olefins suitable for hydroformylation are disclosed in EP 835234, but many other disclosures in this field may readily be found. The synthesis gas for the Fischer-Tropsch process may be obtained from any carbon containing source, including natural gas, LPG, naphtha, crude oil or any liquid derived therefrom, coal, but also biomass or plastic waste. Coal is particularly suitable because of its abundance. Biomass and plastic waste are particularly suitable because of their low alternative value, which may even be negative under certain circumstances.

The starting materials for the olefin oligomerisation processes mentioned above, but also for the hydroformylation of olefins to produce aldehydes suitable for aldol condensation, may be obtained from fluid catalytic cracking (FCC), from the steam or thermal cracking of gasses such as ethane and propane, of liquids such as liquefied petroleum gasses (LPG), of naphtha, of gasoil or heavier distillate, or even of whole crude. The starting material may also come from oxygenate-to-olefin processes, and from paraffin dehydrogenation processes.

We have found that the content of conjugated unsaturated carbonyl compounds in the olefins from oligomerisation may be reduced by reducing the diene content of the oligomerisation feedstock. We have found that a reduction in the content of conjugated unsaturated carbonyl compounds in the olefins from oligomerisation may also be achieved by reducing the amount of oxygen-containing compounds in the feed to oligomerisation. In this context, water may be considered an oxygen-containing compound, as we have found that it may participate in chemical reactions under oligomerisation conditions.

In one embodiment of the process of the present invention, the olefins used as feed in the oligomerisation process have a low diene content, such as at most 3000 wt ppm, preferably at most 2000 wt ppm, more preferably at most 1000 wt ppm and most preferably at most 500 wt ppm of dienes relative to the total weight of the olefin feed to the oligomerisation process. We have found that a reduced diene content of the oligomerisation feed may lead to a reduced presence of conjugated unsaturated carbonyl compounds in the higher olefins obtained from oligomerisation.

In another embodiment of the process of the present invention, the olefins used as feed in the oligomerisation process have a low content of oxygen-containing compounds, such as at most 1000 ppm by weight, preferably at most 600 ppm by weight, more preferably at most 300 ppm by weight, even more preferably at most 100 ppm by weight, yet more preferably at most 40 ppm wt, even more preferably at most 25 ppm by weight and most preferably at most 20 ppm by weight, on the same basis. Conveniently, water is included in the total of oxygen-containing compounds present in the fresh feed to the oligomerisation process.

In an embodiment, the invention relates to a process for the production of a $C_4$ to $C_{15}$ oxo-alcohol comprising the steps of hydroformylation a $C_3$ to $C_{14}$ olefin, hydrogenating the product of hydroformylation to form the $C_4$ to $C_{15}$ oxo-alcohol, and distilling the product alcohol from the hydrogenation product. In another embodiment, the $C_4$ to $C_{15}$ oxo-alcohol is produced by a process comprising the steps of hydroformylating a $C_2$ to $C_4$ olefin to form a $C_3$ to $C_5$ aldehyde, aldolising the $C_3$ to $C_5$ aldehyde in at least one aldol step to a dimer, trimer or tetramer thereof, which is a branched $C_6$ to $C_{15}$ aldehyde, hydrogenating the branched $C_6$ to $C_{15}$ aldehyde to a branched $C_6$ to $C_{15}$ alcohol and distilling the product alcohol from the hydrogenation product. In this last embodiment, the starting olefins are $C_2$ to $C_4$ olefins, and their hydroformylation products are typically not affected by the presence of conjugated unsaturated carbonyl compounds in the olefin feeds. The quality of the alcohol products from such process may be affected by conjugated unsaturated carbonyl compounds that may be made during the hydroformylation, that form during the aldol condensation and that may further be formed during, or remain after, the hydrogenation step. Such conjugated unsaturated carbonyl compounds are difficult to remove by separation, such as a distillation step downstream of the hydrogenation.

The chemical nature of the conjugated unsaturated carbonyl containing compounds with which the present invention is concerned, depends upon the nature of the olefinic feed and the conditions to which it is subjected during oligomerisation, hydroformylation and aldol condensation. However, we have found that the materials that have a strong adverse impact and cause colour formation in the alcohols under acid conditions may be of the following formula, in particular when $R_1$ is hydrogen.

In this formula $R_1$, $R_2$, $R_3$ and $R_4$ may individually be selected from hydrogen and $C_1$ to $C_7$ hydrocarbon groups, particularly branched hydrocarbon groups, providing that $R_1$, $R_2$, $R_3$ and $R_4$ together contain from 2 to 7 carbon atoms. The unsaturated carbonyl containing compounds are usually mixtures of aldehydes and ketones. Ketones in which $R_1$ is a $C_1$ to $C_7$ hydrocarbon group tend to predominate, although the aldehydes in which $R_1$ is hydrogen tend to have the greatest adverse impact on colour formation. Some of the groups $R_1$, $R_2$, $R_3$ and $R_4$ may together form certain cyclic structures.

The presence of these conjugated unsaturated carbonyl compounds in both the olefin and the alcohol may be detected by Gas Chromatography Mass Spectrometry (GCMS). The presence and content of the conjugated unsaturated carbonyl compounds in the alcohol may also be measured by ultra violet spectrophotometry, where the conjugated unsaturated aldehydes absorb strongly at a wavelength in the region of 220-240 nm and the conjugated unsaturated ketones at around 200-220 nm. The presence and content of the conjugated unsaturated carbonyl compounds in the olefin may be determined by adsorption of these compounds from the olefin on silica gel, eluting the absorbed material with a polar solvent from the silica gel, and determining the presence of conjugated unsaturated carbonyl compounds in the polar solvent, such as by GCMS or by measuring the absorption of the eluted material by ultra violet spectrophotometry in the same wavelength regions as specified before. For the purposes of this invention the measurement on the olefin should be made on the product to be fed to the hydroformylation reactor and the measurement on the alcohol should be made on the product that is ready for esterification and which has been obtained after whatever finishing operations that are typically employed.

UV spectrophotometry was found to be a very suitable technique to quantify traces of conjugated unsaturated aldehydes and/or ketones in alcohols. We have found it to be much more sensitive and specific than any other available technique; much lower levels of these compounds can be determined by this technique than with the other available techniques. It was found easy to calibrate to give quantitative results down to very low levels. It is simple to apply and has a fast response time, such that it is suitable for at-line or even on-line application in a chemical process. The results may be readily expressed in milli-equivalents per weight unit of sample, such that the result is readily comparable to the result of a carbonyl number method such as disclosed in US 2006/0105465, which allows an independent monitoring of unsaturated conjugated aldehydes and/or ketones and other compounds containing a carbonyl function.

The content of these conjugated unsaturated aldehydes and ketones was found to be directly proportional to their absorbance at their peak maxima at around the wavelengths in the UV region given before. We found that this relationship follows Beer-Lambert's law:

$$A = \epsilon \times p \times C$$

wherein A is the absorbance
  $\epsilon$ is the extinction coefficient
  p is the path length, and
  C is the concentration.

Provided the path length is known, the extinction coefficient may be determined from testing the absorbance of synthetically prepared blends with known concentrations. On a plot of absorbance against concentration, this was found to show a straight line. Its slope, easily calculated using linear regression, is then equal to $\epsilon \times p$. From this product, the extinction coefficient is determined by dividing by the known path length. In order to cover a large concentration range, different path lengths may be used, and longer path lengths afford to measure lower concentrations. We used cells having nominal path lengths of 1 cm, 0.1 cm, 0.02 cm and 0.001 cm, and were able to obtain excellent correlations, and useful results, down to levels of around 2 ppm by weight of unsaturated compounds having the same carbon number as the alcohol, which represents in a C9 alcohol a concentration of conjugated unsaturated carbonyl functions of 0.02 meq/kg or 0.00002 meq/g, which would represent a contribution to the carbonyl number of 0.4 mg KOH/kg or 0.0004 mg KOH/g. One should realise that the path lengths of the cells are typically known as "nominal" path lengths, and in reality may deviate somewhat from this number. This deviation may influence the calculated extinction coefficient, so that the resulting extinction coefficient is preferably only used for the particular cell it is determined for, and each cell is preferably calibrated individually, using known synthetic blends. The path length may also be determined with a higher accuracy, such as by calibration using known high purity standards containing known concentrations of a compound of which the extinction coefficient is known.

For convenience, the technique is preferably calibrated in functionality, e.g. in milli-equivalents per gram or per kilogram sample (meq/g or meq/kg), or related to the carbonyl function in the measured functionality, which may be expressed also in meq/g or meq/kg, but is even more traditionally expressed in mg KOH per gram. Such a calibration provides a more accurate reading in case a carbonyl containing compound contributing to the reading has an unidentified number of carbon atoms or molecular weight. It is then also directly comparable to the result of the test for total carbonyls, which is typically done in parallel. A carbonyl functionality expressed in milli-equivalents may be converted into a carbonyl number expressed in mg KOH by multiplying the value expressed in milli-equivalents with the molecular weight of KOH, for which typically a value of 56.1 g/mole is used.

We have found that this technique is less suitable for measuring small traces of conjugated unsaturated aldehydes and/or ketones in streams that contain significant amounts of carbon-carbon double bonds. This is because the C=C bond absorbs at around a wavelength of 180 nm, and if this absorption peak is large, as it may be in highly olefinic streams, the shoulder of the olefin absorption peak becomes relatively wide and may hide any small peak of conjugated unsaturated aldehydes and/or particularly ketones, which are expected at the wavelengths of respectively around 230 and 210 nm.

We have found that this difficulty with determining conjugated unsaturated carbonyl compounds in hydroformylation feed or other olefinic streams may be overcome by the following indirect quantification method:

(i) the sample is first passed over a volume of a suitable adsorbent for polar compounds, such as silica gel, sufficient to adsorb the conjugated unsaturated carbonyl compounds;

(ii) any olefins remaining on the adsorbent are then washed out with a non-polar washing liquid, which may be an alkane, such as n-heptane, suitably chosen for not interfering with the rest of the analytical technique;

(iii) the adsorbed conjugated unsaturated carbonyl compounds are then eluted from the adsorbent with a suitable polar eluent, such as ethanol, again suitably chosen for not interfering with the measurement;

(iv) the concentration of conjugated unsaturated aldehydes and ketones in the eluent may then be determined by the UV method described before;

(v) by using known weights of starting sample and eluent, the concentration of the conjugated unsaturated aldehydes and ketones as measured in the eluent may be readily back-calculated to a concentration in the olefinic stream.

The amount of starting sample, adsorbent, and polar eluent used in this indirect method may be suitably selected, together with selecting an absorption cell with a suitably long path length, to give a reading accurate to the second significant digit and to give a detection limit of 0.02 meq/kg, also for this indirect method. We have found that the 1 cm cell may provide the desired capabilities.

We prefer to test the non-polar washing liquid for step (ii) as such in the UV method, to establish it is clean of potentially interfering compounds. We have also found that it is preferable to use a very pure polar eluent as solvent in step (iii), such as ethanol pro-analyse. We prefer to use the same polar eluent or solvent as the blank in the UV measurement, such that any UV signal of the eluent or solvent itself is removed from the background signal.

We have found that in the UV spectrophotometry method according to the invention, conjugated dienes present in the sample have a UV absorption at a wavelength of about 225-230 nm, and may thus interfere with the measurement of the conjugated unsaturated carbonyl compounds, in particular with the conjugated unsaturated aldehydes. We have also found that conjugated dienes show some polarity, and have a tendency to at least partially also adsorb on a strong polar adsorbent such as silica gel. However, we have found that conjugated dienes that have adsorbed on the polar adsorbent in step (i), may be washed out again by the non-polar washing liquid in step (ii), albeit typically after the olefins have been washed from the adsorbent. The amount of non-polar washing liquid required for removing any conjugated dienes from the adsorbent, such that interference with the measurement of the conjugated unsaturated aldehydes and ketones is avoided, may be readily determined by the person skilled in the art. The risk for interference may be further reduced by a suitable selection of an adsorbent that may be more selective to the conjugated unsaturated carbonyl compounds, such as by selecting a molecular sieve or a zeolite with a more appropriate polarity, preferably a lower polarity.

Conjugated dienes or high concentrations of olefins are less likely to be found in alcohol samples. Therefore, although the indirect method may be applied to alcohol samples, such extra effort may typically be dispensed of.

We have found that the content of the conjugated unsaturated carbonyl compound in the olefin may be reduced by adsorption over an adsorbent with an affinity for polar compounds, particularly over molecular sieves, zeolites, activated carbon, activated alumina, silica, and especially over silica gel. The adsorption may be performed by pushing the olefin feedstream, or letting it flow by gravity, through a bed of the adsorbent. The feedstream is preferably liquid, and lower temperatures favour the adsorption of the trace compounds on the adsorbent. When breakthrough is occurring, as measured by the above analytical method, the adsorbent bed is preferably taken out of service. The used adsorbent may be discarded, or regenerated. A suitable regeneration may be done by eluting or washing the adsorbed polar compounds from the adsorbent by the use of a polar solvent, such as an ester, a ketone or an alcohol, in particular ethanol and preferably methanol, but acetone or methyl ethyl ketone (MEK) may also be used. We prefer to use a solvent that does not interfere with the UV measurement of the present invention. A suitable solvent may be the heavy oxonation fraction (HOF) from the alcohol production process. It brings the advantage that traces of this solvent left on the adsorbent may not need to be removed, as they may be allowed to pass together with the olefin into the hydroformylation step and may be recovered in a downstream distillation step such as in the bottoms of the final tower in the alcohol distillation. Methanol may be preferred as the solvent because of its low cost, and its ease of evaporation from the adsorbent. The polar solvent may be separated from the eluted polar compounds and recovered by means such as distillation. Methanol may also be preferred for its ease of separation from the extracted conjugated unsaturated carbonyl compounds, preferably including recovery and its reuse for regenerating more adsorbent. The polar solvent remaining on the adsorbent may be removed by flushing with a warm or hot gas or vapour, upon which the dried adsorbent may be ready for reuse in adsorption service.

We have also found that the content of the conjugated unsaturated carbonyl compound in the olefin may be reduced by providing less oxygen-containing components to the oligomerisation process. We have observed that oxygen-containing compounds present in the oligomerisation feed, such as water, alcohols such as methanol, ethanol, propanol, isopropanol and the various butanols, but also ethers such as di-isopropyl ether, may lead in oligomerisation processes such as those using solid phosphoric acid and/or molecular sieve or zeolite catalysts, to the formation of other oxygenates in the oligomerisation product. We have found that some of these oxygenates formed may be conjugated unsaturated carbonyl compounds, more typically conjugated unsaturated ketones. We have found that the concentration of such conjugated unsaturated carbonyl compounds in the products from the oligomerisation process may be lowered by reducing the amount of oxygen-containing components entering the oligomerisation process.

The content of the conjugated unsaturated carbonyl compound in the alcohol may also be reduced by subjecting the hydrogenation product to the adsorption treatment. US 2006/0129004 discloses a process comprising the treatment of an aldehyde-containing organic phase, which was derived from a hydroformylation reaction and after its treatment for the conversion of the cobalt hydroformylation catalyst into water soluble cobalt(II) salts and the separation thereof, with an adsorbent such as silicon dioxide. The adsorbent is claimed to adsorb from the aldehyde-containing organic phase the traces of cobalt, which in their metal salt form are very polar compounds having a high affinity for the adsorbent. The stream that is treated is abundantly rich in aldehydes, which are also relatively polar, and contain dissolved water, which is also polar. We believe that, in the adsorption treatment disclosed in US 2006/0129004, conjugated unsaturated carbonyl compounds have insufficient polarity difference in a stream matrix in which there is such an abundance of other and more polar compounds, in order to be preferably adsorbed on such adsorbent. For this reason we propose to treat the product of hydrogenation, because the alcohol matrix has a lower polarity than aldehydes, and any cobalt compounds are believed not to pass the typical fixed bed catalytic hydrogenation step. We have also found that the conjugated unsaturated carbonyl content of the alcohol may be reduced by very fine distillation of the alcohol. We have found that a major portion of conjugated unsaturated carbonyl compounds present in the product from hydrogenation may be removed by distilling a light byproduct fraction away from the alcohol, such as when a light oxonation (or "oxo") fraction (LOF) is separated from the alcohol. The number of theoretical fractionation stages and reflux ratio that is required to obtain an acceptable separation may be readily determined by the person skilled in the art, by using the UV method of the present invention for guidance. We prefer to limit the amount of total oxygenates into such a LOF fraction to at most 2% by weight, preferably at most 1.5 wt %, more preferably at most 1.0 wt % and most preferably at most 0.5 wt %, such that the LOF by-product may be readily accepted as a component for a refinery motor gasoline pool.

A major portion of the conjugated unsaturated carbonyl compounds present in the product from hydrogenation may be removed by distilling a light byproduct fraction away from the alcohol. Removal of residual conjugated unsaturated carbonyl compounds may then conveniently be performed by adsorption on the alcohol stream that is distilled from the product of hydrogenation, after separation of light byproducts and preferably also of heavy byproducts. This brings several advantages, including that the stream to be treated is smaller in volume than when the entire product is treated, and that the adsorption process is more efficient because most of the conjugated unsaturated carbonyl compounds have already been removed together with the separation of the light byproduct fraction in distillation, typically the first distillation tower.

In another embodiment, the level of conjugated unsaturated carbonyl compounds may be reduced by hydrogenation. This hydrogenation step is preferably carried out as an extra hydrofinishing step, preferably after separating the alcohol from the light oxonation fraction and the heavy oxonation fraction by distillation as discussed above, or directly after the hydrogenation step. We have found that a nickel-containing catalyst, such as Calsicat 475RS is capable of hydrogenating these compounds down to very low levels and reduce their content to acceptable levels according to the present invention. Preferred hydrofinishing conditions are a hydrogen partial pressure of 40-70 barg, typically about 55 barg, and a temperature in the range of 60-120° C., more preferably 80-110° C. Preferably, the process uses a weight hourly liquid space velocity (WHSV) of 3 to 4, expressed e.g. in kg of liquid feed per kg of catalyst, and a hydrogen feed of 2 $Nm^3$ per $m^3$ of liquid feed.

We have also found that a Pd containing catalyst, such as Pd on carbon, is able to selectively hydrogenate the C=C double bond in the conjugated unsaturated carbonyl compound and convert the compound into the corresponding carbonyl compound without the conjugated unsaturated double bond. Such hydrogenation step over a supported Pd catalyst may advantageously be performed at mild conditions, such as 6 barg of hydrogen pressure and at a temperature of 110-120° C. This selective hydrogenation step, which may be operated as at least a part of the extra hydrofinishing step, or at the end of the hydrogenation step, such as downstream of a nickel-based hydrogenation treatment, has at least the advantage of a lower exotherm compared to a step that saturates both double bonds in the molecule. It also causes less dehydration and produces less byproduct, making it very suitable for a treatment of the already distilled alcohol.

The conjugated unsaturated carbonyl compounds may be derived from a variety of side reactions throughout the alcohol production processes and their nature depends upon the technology that is used. For example in the "low pressure" process that is used for the production of 2-ethylhexanol, 2,4-dimethylheptanol or 2-propylheptanol, lower olefins (ethylene, propylene and/or butene) are hydroformylated usually with a rhodium catalyst into the corresponding aldehyde. This can result in side reactions producing conjugated unsaturated carbonyl compounds known as acroleins. These acroleins may affect the quality of the alcohol that is derived by hydrogenation of the aldehyde, such as n-propanol, n-butanol, isobutanol, n-pentanol or 2-methyl butanol. In this process, the aldehyde that is produced in the hydroformylation process may later be subjected to at least one aldol condensation which produces conjugated unsaturated carbonyl compounds. The product of the aldol condensation may then be subjected to hydrogenation, in order to remove both the ethylenic unsaturation and the carbonyl group. However, such hydrogenation may not be successful in the removal of all the unsaturation. Accordingly, in the low pressure technology, conjugated unsaturated carbonyl compounds can be present in the $C_3$ or higher carbon number alcohol of this process (typically a $C_4$, $C_5$ alcohol if no aldolisation step is practised, and typically a $C_8$, $C_9$ or $C_{10}$ alcohol when the process includes an aldolisation step) as a result of side reactions in the hydroformylation and/or because of incomplete hydrogenation.

In the high pressure oxo technology, which is typically used for the production of $C_6$ to $C_{15}$ alcohol mixtures, lower olefins may first be oligomerised to obtain higher olefins. The product of the oligomerisation is then later subjected to high pressure hydroformylation (usually with a cobalt or a rhodium catalyst) and the product of hydroformylation is hydrogenated, typically to convert at least the major portion of the alcohol precursors to alcohols. The hydrogenation product may then be separated by fractional distillation into a light fraction (also known as light oxonation fraction or LOF), typically comprised of hydrocarbons, the desired alcohol product, and a heavy fraction (also known as heavy oxonation fraction or HOF). The distilled alcohol may then optionally be subjected to a hydrofinishing treatment, as disclosed above. The prime purpose of this hydrofinishing treatment may be to reduce total carbonyl content, but a secondary purpose may be to also reduce the content of conjugated unsaturated carbonyl compounds in the product alcohol. We have found that such hydrofinishing step may be operated such that little to no by-products are formed, and that the inclusion of an extra separation step for separating such light or heavy byproducts may not be needed. It is preferred however, that dissolved hydrogen be removed from the hydrofinishing product, such that explosion risks and other safety problems in alcohol storage tanks and shipments may be avoided. Therefore the hydrofinished alcohol is preferably stripped with an inert gas, such as nitrogen, before the alcohol is stored or shipped. In this process, conjugated unsaturated carbonyl compounds may be present in the original olefin feed; they may also be formed by side reactions (such as oxidation or others as described before) during the oligomerisation process; they may be formed from impurities such as dienes that may be present in the olefin feed or that may be formed during oligomerisation; they may be formed during hydroformylation and/or during removal of the hydroformylation catalyst, where side reactions such as acrolein formation, aldolisation, cracking, oxidation or reaction of some residual non-oligomerised olefins may occur; or they may be caused by the high temperatures practised in the reaction and/or the separation steps. They may also be formed when the heavy by-products from the alcohol production are subjected to a decomposition treatment (so-called HOF "cracking", performed for recovery of extra useful product or precursors and possibly recycling of these extra useful molecules into the alcohol manufacturing process, preferably into the hydrogenation step), such as by treatment of the HOF at temperatures of 300° C. and above over an activated alumina catalyst.

Whilst the present invention is primarily concerned with alcohols and olefins having a reduced level of conjugated unsaturated carbonyl compounds, particularly conjugated unsaturated aldehydes, it may also be important that the overall carbonyl content of both the alcohol and olefin not exceed 10 meq/kg (about 0.5 mg KOH/g), preferably 7.0 meq/kg, more preferably 5.0 meq/kg and most preferably 3.57 meq/kg (0.2 mg KOH/g). Accordingly the invention further provides an alcohol having an overall carbonyl content of at most 10 meq/kg and a level of conjugated unsaturated carbonyl compounds according to the levels already specified.

Because the current invention is very specific to conjugated unsaturated carbonyl compounds, which, unlike other carbonyl compounds, were found to be particularly strong colour contributors in the esterification process, the alcohols of the present invention may contain a measurable level of other carbonyl compounds that are acceptable for the downstream use. These other carbonyl compounds may for example be present at a level of at least 0.17 meq/kg, preferably at least 0.20 meq/kg or 0.35 meq/kg, more preferably at least 0.50 meq/kg or 0.88 meq/kg, even more preferably at least 1.05 meq/kg or 1.20 meq/kg, and yet more preferably at least 1.50 meq/kg. These alcohols still provide at least the advantages mentioned before, but they do not require the number and selection of purification processes that may be required to achieve carbonyl contents below the levels specified here.

Hydroformylation is a well-known process in which an olefin is reacted with carbon monoxide and hydrogen in the presence of a catalyst to form aldehydes and alcohols containing one carbon atom more than the olefin feed. This process has been operated commercially for many years and there have been two principle technology families used. The first technology family is known as the low pressure oxo process family, as it operates at pressures from 10 to 100 bar gauge, typically from 15 to 50 bar gauge and generally involves the use as catalyst of an organometallic complex of rhodium with an organophosphorous ligand, for providing the necessary catalyst stability at the lower pressure. The second process family is known as the high or medium-pressure process family and generally involves the use of a cobalt or rhodium based catalyst and typically operates at pressures from 100 to 350 bar gauge, preferably from 150 to 320 bar gauge. Suitable high pressure hydroformylation processes are described in WO 2005058787, PCT/EP2008/053718 and PCT/EP2008/053783, the content of which is herewith incorporated by reference. Generally the low pressure processes are used for the hydroformylation of unbranched and terminal, primarily lower olefins such as ethylene, propylene and n-butenes, but also including n-hexene-1 and n-octene-1 and more recently also mixtures of slightly branched but primarily terminal olefins obtained from the Fischer-Tropsch process, such as explained in EP 835234, the content of which is herewith incorporated by reference. The high or medium pressure processes on the other hand are primarily used for the hydroformylation of mixtures of linear and branched primarily internal olefins such as those containing 5 or more carbon atoms. Both processes are widely used to produce what are known as "higher alcohols" or aldehydes or acids which are in the $C_6$ to $C_{15}$ range particularly the $C_9$ to $C_{13}$ range.

Suitable hydrogenation techniques for hydrogenation of the hydroformylation products and/or the hydrogenation of the products from the aldolisation of the aldehydes made by hydroformylation are described in WO 2005058782, the content of which is herewith incorporated by reference.

We have found that, if the content of a conjugated unsaturated carbonyl compound in an alcohol is reduced to below 0.18 meq/kg, then alcohols having a Hot Sulphuric Acid Colour below 25 on the Platinum-Cobalt Colour scale, according to ASTM D E 852-94a (sometimes also referred to as Hazen colour or APHA colour) as measured on a Lovibond PFX 990/P Petrochemical Tintometer, may be obtained. Equivalents to this test are ASTM D5368 using a spectrophotometer instrument, E 313 and ASTM 1209 using colour tubes, and BRCP 4273. In particular we have further found that products having a Hot Sulphuric Acid Colour in the range 7 to 20, more particularly 8 to 15 and even more particularly 9 to 14 on the aforementioned Pt/Co colour scale may be obtained. This is particularly useful with $C_6$ to $C_{15}$ alcohols which are to be used for esterification using strong acid catalysis, particularly for the production of plasticiser ester and synthetic lubricants.

Accordingly the present invention further provides a branched $C_6$ to $C_{15}$ alcohol having an ASTM E 852-94a Hot Sulphuric Acid Pt/Co Colour below 25, particularly below 20 and in the range 7 to 20, whereby, (i) if the alcohol is a mixture having a nominal average carbon number of 9, the alcohol has an ASTM E 852-94a Hot Sulphuric Acid Colour below 20, and (ii) if the alcohol is a mixture having a nominal average carbon number of 10, the alcohol has an ASTM E 852-94a Hot Sulphuric Acid Colour below 14.

Preferably all branched alcohols of the current invention have an ASTM E 852-94a Hot Sulphuric Acid Colour below 20, and more preferably below 14.

In a further embodiment, the present invention provides an ester of a carboxylic acid and a branched $C_6$ to $C_{15}$ alcohol, the alcohol having an ASTM E 852-94a Hot Sulphuric Acid Pt/Co Colour below 25, particularly in the range 7 to 20, whereby, (i) if the alcohol is a mixture having a nominal average carbon number of 9, the alcohol has an ASTM E 852-94a Hot Sulphuric Acid Colour below 20, and (ii) if the alcohol is a mixture having a nominal average carbon number of 10, the alcohol has an ASTM E 852-94a Hot Sulphuric Acid Colour below 14. Preferably the ester is of a branched alcohol having an ASTM E 852-94a Hot Sulphuric Acid Pt/Co Colour below 25, preferably below 20, and more preferably below 14.

Examples of alcohols to which the present invention is applicable include saturated monohydric aliphatic alcohols such as normal- and iso-hexanol, normal- and iso-heptanol, normal- and iso-octanol, 2-ethylhexanol, normal- and iso-nonyl alcohol, 2,4-dimethylheptanol, normal- and iso-decanol, 2-propylheptanol, normal- and iso-undecanol or dodecanol and normal- and iso-tridecanol.

The acid or anhydride employed in the production of the esters from the alcohols of the invention is preferably organic. Examples of organic acids or anhydrides that may be used in the esterification reaction include aromatic monocarboxylic acids, such as benzoic acid; polybasic aromatic carboxylic acids or anhydrides thereof, such as phthalic acid, phthalic anhydride, isophthalic acid, terephthalic acid, trimesic acid, trimellitic acid, trimellitic anhydride, pyromellitic acid and pyromellitic anhydride; monobasic carboxylic acid such as acetic acid, pivalic acid, cyclohexanoic acid, acrylic acid and methacrylic acid, polybasic(cyclo)aliphatic carboxylic acids such as adipic acid, 1,2-cyclohexane dicarboxylic acid, 1,3-cyclohexane dicarboxylic acid, 1,4-cyclohexane dicarboxylic acid, sebacic acid and azelaic acid and citric acid; polybasic unsaturated aliphatic carboxylic acids such as maleic acid and fumaric acid; and aliphatic monocarboxylic acids such as oleic acid and stearic acid. The various phthalic acids or anhydrides are preferred. The alcohols employed in the esterification may be used singly or in combination, as required. $C_6$ to $C_{13}$ alcohols are preferably used to make plasticiser esters, and the $C_9$ to $C_{11}$ alcohols, especially the $C_{10}$ and $C_{11}$ alcohols, are preferred especially in the production of plasticiser esters.

The esterification reaction preferably employs an organic metal compound catalyst. Examples of such catalysts include alkyl titanates such as tetra-isopropyl titanate, tetra-n-butyl titanate, titanates having a mixture of butyl and isopropyl groups, or tetra-iso-octyl titanate, or organic tin compounds such as tin oxalate, tin octanoate or tin maleate, that exhibit a catalytic activity at an esterification reaction temperature. Suitable esterification processes are described in WO2005021482, WO2006125670, PCT/EP2008/001837 and PCT/EP2008/001838.

In one embodiment of the process, the esterification reaction is conducted by adding an alcohol to an organic acid or its anhydride, and reacting the mixture, typically at a temperature in the range of 140-230° C. but possibly even lower, such as down to 120° C. when using sulfuric acid or para-toluene sulphonic acid (pTSA) as the catalyst to improve ester colour. Preferably the esterification is carried out at from 150° C. to 230° C., more preferably from 160° C., 170° C. or 180° C. upwards, and even more preferably at least 185° C., when using a titanate catalyst. When using an organometallic catalyst, esterification is preferably carried out for 1 to 4 hours in an inert gas atmosphere while removing water formed. The reaction time is more preferably at the lower end of the range, e.g. from 1.5 to 2 hours, and optimally even less than 1.5 hours. After the esterification, typically a base and water, preferably in the form of an aqueous base, is added to the resulting reaction solution to neutralise any unreacted acid and/or mono-ester and/or catalyst, and to hydrolyse the catalyst, if this is organometallic. It is also preferred to remove any free water after the crude ester has been treated with the base and before filtration, particularly if the treatment has been with aqueous base. Preferred bases include alkali metal salts, particularly sodium salts, such as sodium carbonate, and alkali metal hydroxides, such as sodium hydroxide, e.g. aqueous sodium hydroxide. Any excess alcohol is typically recovered by stripping (which advantageously removes alcohol, water and other light materials) and the resulting ester product is then purified to obtain a plasticiser.

After esterification, the crude ester typically contains contaminants and requires purification. These contaminants may belong to the family of acidic residues, unreacted alcohol, catalyst residues, water and the contaminants that were already present in the feed alcohol feed, most of these being so-called monomeric components that are eluted in the so-called "light ends" region of the plasticiser Gas Chromatogram or GC-spectrum, around the unreacted alcohol, as discussed in WO2005021482, the contents of which are herewith incorporated by reference. The crude esters may also contain by-products, such as alcohol(di-alkyl)ethers, benzoate esters, mono-esters from dibasic acids, alcohol oxo acid esters, hemiacetals and vinyl ethers (these are so-called dimeric components and are often collectively called "ethers" or "intermediates" due to their elution in the plasticiser Gas Chromatogram or GC-spectrum between the monomeric light ends and the "trimeric" diesters). Many of these dimeric materials, as well as acetals which are "trimeric" compounds, may become hydrolysed during later stages in the process to form odour formers such as aldehydes and/or other light ends. Suitable methods for the purification treatment of the esters are described in WO 2005021482 and WO 2006125670, the contents of which are herewith incorporated by reference.

The present invention is illustrated by reference to the accompany Examples in which material were prepared and tested in the following manner.

Experimental Section

1. METHODS a) Ultra Violet Spectrophotometer Testing.

The purpose of this test is to record the light absorption spectrum of a diluted or non-diluted sample in the ultra violet (UV) range of the light spectrum. A UV/VIS recording spectrophotometer of the type Hewlett Packard model 8452A was used. The apparatus was equipped with a deuterium lamp for measurement in the range from 190 to 340 nm and a direct light sample compartment to measure the light that goes straight through the sample, without being absorbed or diffracted.

A quartz flow through cell was used (available from Hellma) with a path length selected for the concentration range that is expected, such that the absorbance measured at the peak level, represented by A in Beer-Lambert's law discussed hereinbefore, is between 0.1 and 1.5. A range of cells having a nominal path length of 0.01 mm, 0.2 mm, 1 mm and 1 cm was found useful to cover a wide range of concentrations by this technique. The range of analysis can be extended into higher concentrations by diluting the sample to be measured, e.g. 10 or 100 times, in a diluent, such as a carbonyl free alcohol (e.g. methanol or ethanol) or hydrocarbon (e.g. hexane), depending on the polarity of the sample.

Before starting the analysis, the lamp was allowed to warm up for 30 minutes. The spectrophotometer was set for the direct light measurement with a medium scan speed and a slit width of 2.0 nm. Each sample analysis was performed against a blank. For non-diluted polar samples, an alcohol was used as blank: analytical grade ethanol was used as blank for the samples of ethanol extract obtained as eluent after adsorption of conjugated unsaturated carbonyl compounds from olefin samples; for samples of alcohols having a carbon number according to the invention, a purified version of the same alcohol was used as the blank in the test. This avoids the creation of extra UV absorption peaks of the sample vs. the blank, such as when an isononyl alcohol sample is tested using an ethanol blank.

Before performing the analysis, the empty cuvette was cleaned thoroughly with analytical grade methanol or isopropanol for polar samples and with hexane for non-polar samples. The cuvette was then blown dry using dry compressed air. The absorbance of the empty cuvette was measured, each time before and after sample analysis to verify it had been cleaned properly. The cleaning procedure should be repeated if the absorption reading taken for the cleaned cuvette, when containing a blank, does not correspond to the expected base line signal value plus minus 5%. If the cuvette contained a sample with a high UV absorption in the relevant region, an additional reading of the blank was performed to verify there was no remaining contamination from the previous sample in the cell.

When desired, a calibration curve for each cell, and separately for the conjugated unsaturated aldehydes and for the ketones, may readily be determined as explained hereinbefore. The exact path length of the cell may, if needed, be determined by testing a known sample containing a known concentration of a compound of which the extinction coefficient is accurately known.

The amount of conjugated unsaturated aldehydes is given by the height of the peak in the range 220-240 nm, typically at about 230 nm, and the amount of conjugated unsaturated ketones is given by the height of the peak in the range 200-220 nm, typically at about 210 nm. It should be realised that the wavelengths at which the peaks for the conjugated unsaturated carbonyl compounds occur in the UV spectrum may move slightly under the influence of other carbonyl functions present in the sample being tested. The peaks may therefore not always show exactly at the same wavelength.

Figure 1:
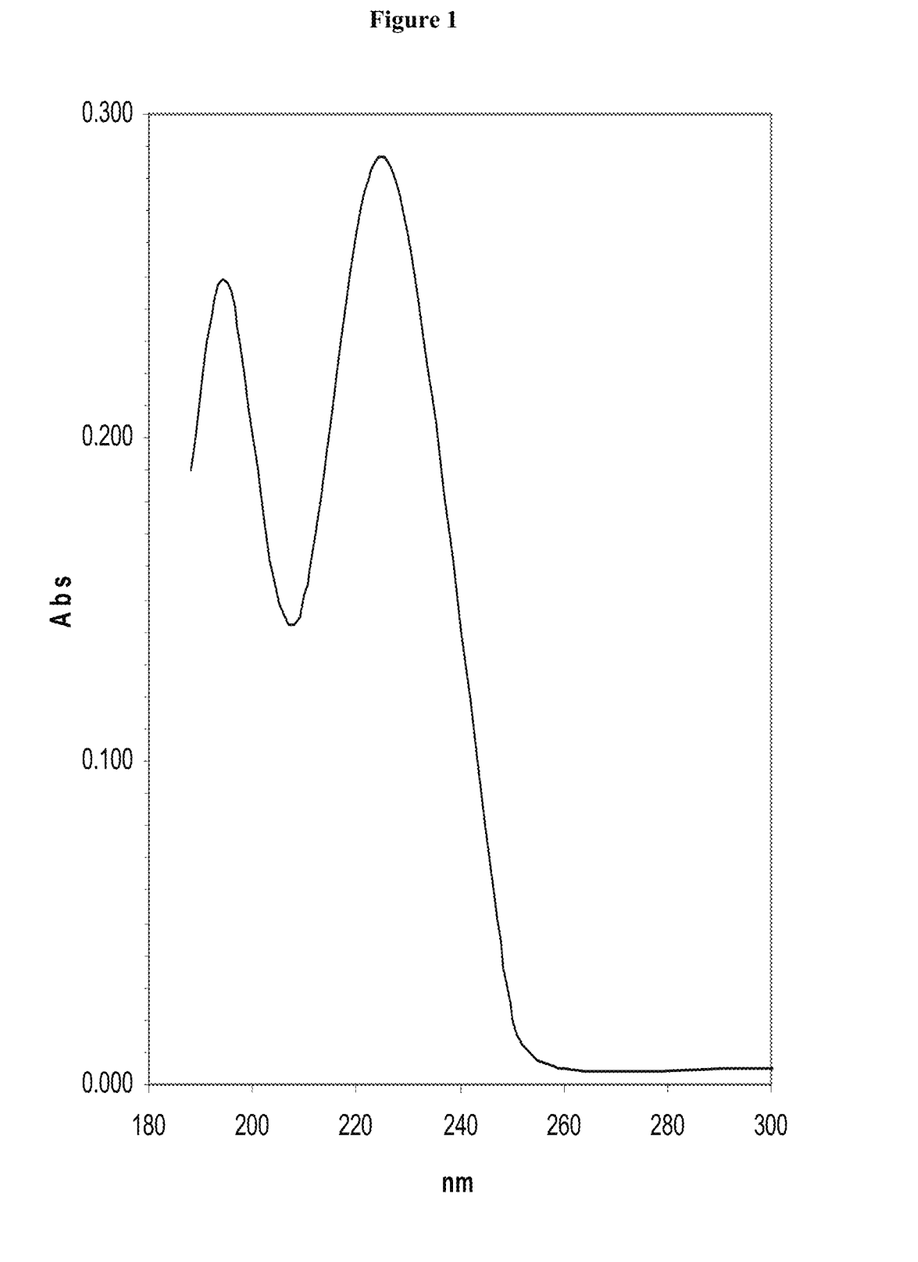
FIG. 1 and FIG. 2 are ultra violet spectra of an isononyl alcohol sample that was spiked respectively with a conjugated unsaturated aldehyde and a conjugated unsaturated ketone.

FIG. 1 shows the UV absorption spectrum in the wavelength range of 180 to 300 nm obtained with a sample of isononyl alcohol, spiked with a trace amount of 2,4-dimethyl-2-heptenal, a conjugated unsaturated aldehyde. The sample was spiked up to a carbonyl number content of 0.0573 mg KOH/g. A cell with a path length of 0.2 mm was used in this test. The conjugated unsaturated aldehyde shows a distinct absorption peak in the range 220-230 nm. In this test, ethanol was used as the blank, and a signal of the isononyl alcohol relative to the ethanol blank shows up around 190 nm.

Figure 2:
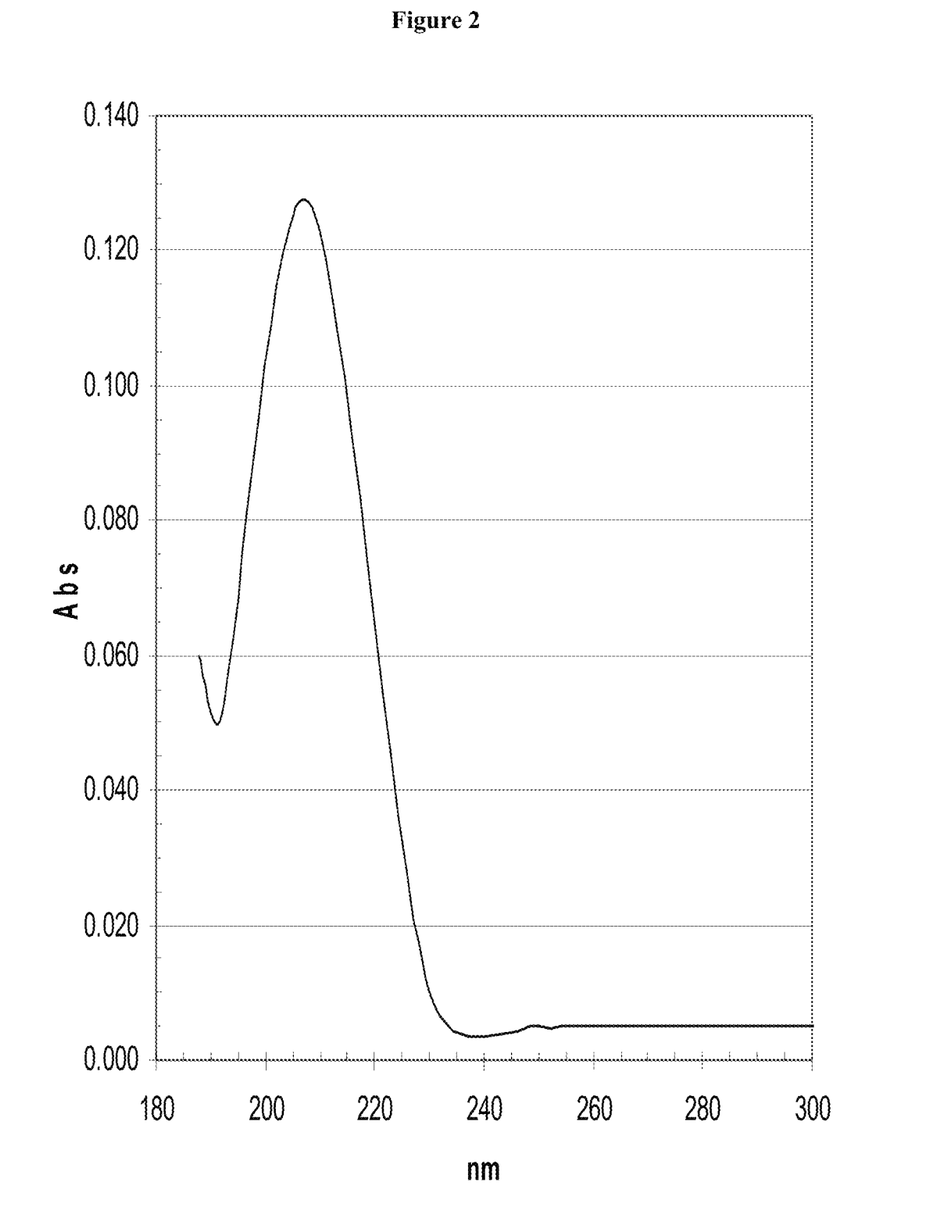

FIG. 2 shows the UV spectrum, in the same wavelength as in FIG. 1, of a sample of isononyl alcohol, spiked with a trace amount of methyl vinyl ketone, a conjugated unsaturated ketone. The sample was spiked up to a carbonyl number content of 0.0514 mg KOH/g. A cell with a path length of 0.2 mm was used. The conjugated unsaturated ketone shows a distinct absorption peak in the range 205-210 nm. In this test, the pure (not spiked) isononyl alcohol was used as the blank, which has caused the absorption signal around 190 nm to disappear into the background signal.

Figure 3:
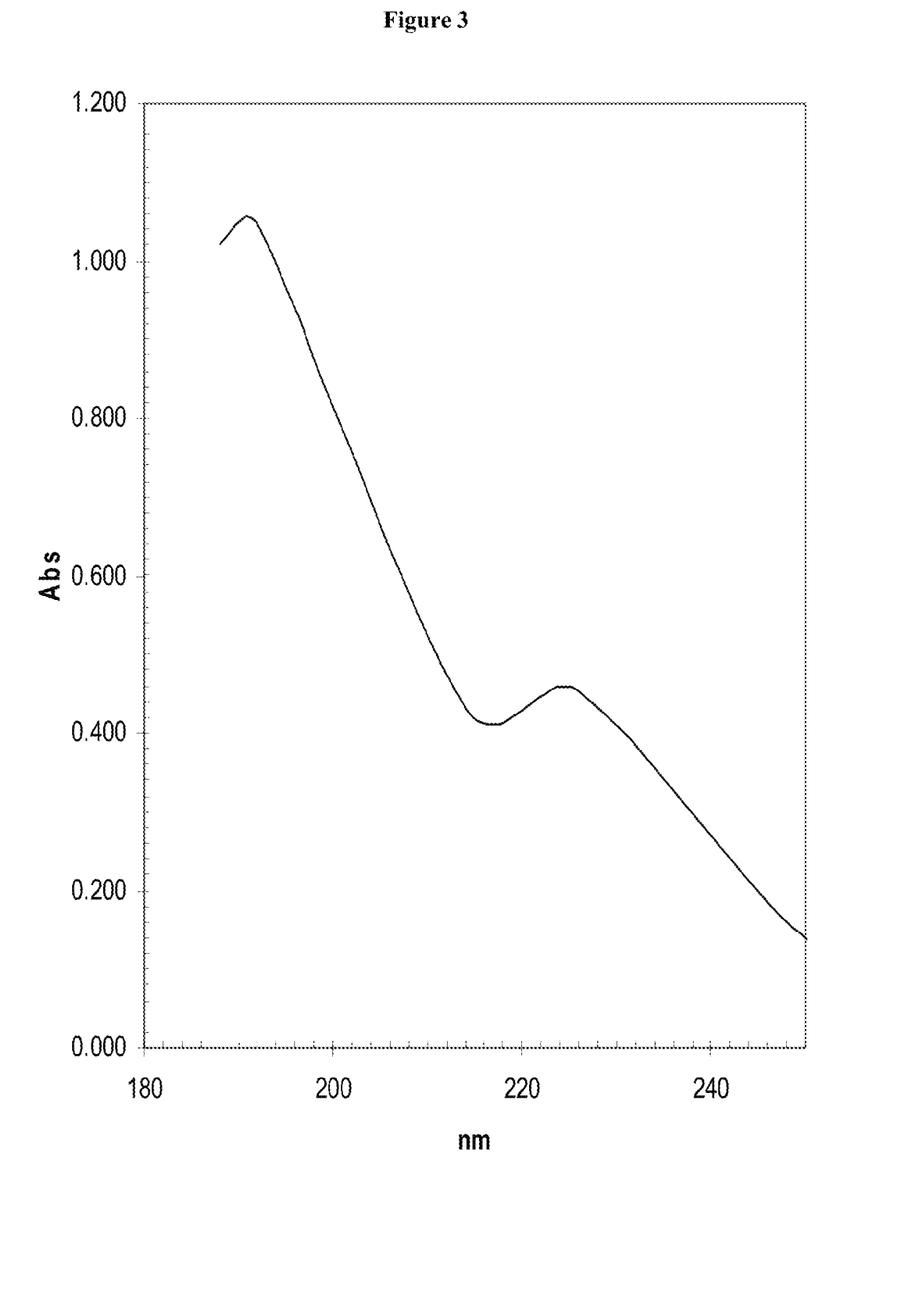
FIG. 3 is an ultra violet spectrum of a product obtained by adsorption from an octene mixture on silica gel, followed by eluting with ethanol, showing the presence of conjugated unsaturated compounds by virtue of an absorption peak at 220-230 nm.

FIG. 3 shows the UV spectrum, in the wavelength of 280 to 250 nm, of the ethanol eluent tested as explained in Example 4 below. The spectrum shows an absorption peak in the range 220-230 nm, which is attributed to conjugated unsaturated aldehydes. The absorption peak around 190 nm is attributed to olefins that had remained on the silica gel after the heptane wash.

b) Carbonyl Content Determination

The total carbonyl content may be given by a conventional carbonyl number technique, such as the reactive method disclosed in US 2006/0105465, the contents of which is herewith incorporated by reference. For example, the carbonyl content may be determined by reacting the sample with 2,4-dinitrophenylhydrazine, followed by addition of potassium hydroxide, and by analysing the resulting mixture by colorimetry, as discussed in this document.

c) Hot Sulphuric Acid Colour Test, Based on ASTM E 852-94a.

This test is similar to the ASTM D 1209-54 test used for colour in U.S. Pat. No. 3,232,848. ASTM D 1209 test has now been superseded by ASTM E 852-94a, and by ASTM D5368, which is a variation of ASTM E 852-94a using a spectrophotometer.

The Hot Sulphuric Acid Colour tests were performed as follows: 50 grams of the material to be tested were placed in a 100 ml erlenmeyer flask. The sample was cooled down in an ice bath during 30 minutes to about +2° C., after which 5.00 ml of concentrated sulphuric acid was introduced from a burette over a period of 1 minute. The erlenmeyer was then placed in an oil bath where it was maintained for 1 hour at 100° C. and immediately replaced in the ice bath until its temperature was lowered to room temperature.

The colour of the sample was measured within ten minutes after the room temperature was reached and the total visible light absorption measurement was made in a Lovibond PFX 9901 P Petrochemical Tintometer using a 10 cm cuvette and employing the Platinum-Cobalt Scale according to ASTM D 1209. We have found that it is important to measure the sample shortly after the sample has reached room temperature in order to obtain reproducible measurements. We have also found that relatively fresh analytical grade sulphuric acid is required for good reproducibility since the measurement is subject to deviation when the $H_2SO_4$ has been exposed to light and air for long periods of time. We have also found that it is preferred to store the samples in the absence of light, most preferably the absence of daylight. This method was repeated 12 times with samples of the same alcohol, and the readings obtained were 20, 22, 23, 25, 23, 23, 23, 24, 22, 23, 23 and 23 on the Pt/Co scale, demonstrating excellent reproducibility of the method.

The examples below show that saturated carbonyl compounds also cause colour formation in this hot sulphuric acid test. It is believed that due to the exposure of the sample to the hot sulphuric acid in this test, some of the carbonyl compounds present in the sample may aldolise and subsequently dehydrate to form conjugated unsaturated compounds. We further believe that these conjugated compounds, together with any conjugated unsaturated compounds already present in the alcohol being tested, may be responsible for forming the colour that then is measured by comparison with the colour standards. A colour formed in this test method may therefore be an indication of the presence of a carbonyl compound, aldehyde or ketones, saturated or unsaturated, conjugated or non-conjugated.

d) Silica Adsorption

Where materials were subject to adsorption over silica, a small known amount of the material (e.g. 32.8 g of octenes) was percolated over a small known amount (e.g. 4.5 g) of adsorbent. We used Silicagel Kieselgel fia fein 0.071-0.16 mm 100-200 mesh DIN 51791-ASTM D1319-58T. For the percolation, a fritted disk (Alltech part #211408) was fitted in an 8.0 ml extract-clean reservoir of 8.0 ml (Alltech part #210208) and the adsorbent was placed over the fritted disk. If the starting material contained significant amounts of olefins (and/or possibly dienes), the olefins (or dienes) remaining on the silica gel after percolation were washed off selectively by washing the silica gel with n-heptane. We have found that polar compounds such as alcohols or ketones are not removed to any significant extent by the heptane wash, even when using ample amounts of heptane, such as 150 ml, and that these polar compounds remain almost quantitatively absorbed on the silica gel. We have also found that olefinic hydrocarbon compounds such as octenes may successfully be removed from the silica gel down to a level at which they do not interfere with the UV method of the invention. The same may be achieved for conjugated dienes when interfering amounts of conjugated dienes are present in the sample to be analysed. The polar products that were adsorbed on the silica were removed therefrom by elution/percolation with a small amount (e.g. 12 grams) of ethanol. We have found that this small amount of ethanol is largely sufficient to remove over 99% of model polar compounds such as alcohols or ketones from a silica gel adsorbent. We have found that olefins do not anymore interfere in the UV absorption measurement if their concentration in the ethanol after elution is at most 1% wt, although this level is dependent on the level of conjugated unsaturated carbonyl compounds that is present.

The eluted ethanol containing the polar components was subjected to GCMS employing a polar column to enable a tentative identification of the oxygen containing species. The GCMS allowed to allocate several peaks to carbonyl components containing further unsaturation.

2. EXAMPLES

Example 1

Samples of a $C_9$ alcohol were spiked with various amounts (i) a laboratory grade pure octene-1 obtained from Acros, (ii) commercial octenes A and B, both used in $C_9$ alcohol manufacture, and (iii) the light oxo fraction (LOF) obtained by fractional distillation of the $C_9$ alcohol produced from commercial octenes B. The pure (not spiked) alcohol had an Iodine value (IV) of 0.0004 and a Hot Sulphuric Acid Colour of 23 on the Pt/Co scale, and the amounts spiked were chosen to reach the indicated target levels. The Iodine values (IV, expressed in mg of iodine per g of sample) of all spiked samples were determined according to ASTM D5768, to give a measure of the olefin content of the spiked mixtures. The Hot Sulphuric Acid Colours of the spiked mixtures were then measured according to the method explained before, with the following results.

| C9 alcohol IV | Hot Sulphuric Acid Colour (Pt/Co scale) Spiked with | | | |
|---|---|---|---|---|
| | Octene-1 | Commercial Octenes A | Commercial Octenes B | LOF (IV) |
| 0.17 | 21 | 26 | 29 | 39 (0.18) |
| 0.20 | 23 | 28 | 31 | 44 (0.25) |
| 0.79 | 23 | 42 | 51 | 118 (0.9) |

These results show that ethylenic unsaturation by itself (as indicated by an increase in Iodine Value) does not necessarily cause a deterioration of the Hot Sulphuric Acid Colour of an alcohol sample. Deterioration is observed with the addition of increasing amounts of commercial octenes, indicating that it is another functionality present in the commercial octenes that contributes to the Hot Sulphuric Acid Colour increase observed in the alcohol sample. For the last column, spiking was done with similar levels of LOF, which is the light byproduct that is separated from the commercial C9 alcohol product by distillation and before hydrofinishing of the alcohol. Without wishing to be bound by theory, we believe that unreactive compounds, present in the octene feed to the alcohol process but remaining unchanged in the process, primarily concentrate in this LOF by virtue of their unchanged boiling points. It is however not excluded that smaller traces of these compounds end up in the alcohol product, which is (derived from) the next heavier distillation fraction of the hydrogenation product. With LOF spiking, a much stronger effect on the Hot Sulphuric Acid Colour is observed for similar levels of ethylenic unsaturation (IV) as in the other spiking experiments. This suggests that the compound in the octene feedstock which may be a contributor when the alcohol derivative product develops a colour in the Hot Sulphuric Acid test, survives the hydroformylation and hydrogenation steps and is retrieved at a concentrated level in the LOF by-product of the alcohol derivative.

Example 2

The LOF used in Example 1 was percolated through a bed of silica gel by the procedure described above, in order to adsorb polar compounds, the resulting liquid was mixed with the $C_9$ alcohol used in Example 1, at levels resulting in the indicated IV values, and the Hot Sulphuric Acid Colour test was again performed according to ASTM 1209 with the following results.

| IV | Hot Sulphuric Acid Colour (Pt/Co scale) |
|---|---|
| 0.17 | 30 |
| 0.20 | 27 |
| 0.79 | 44 |

This example shows that a considerable amount of the materials that caused the colour deterioration up to 118 when using the LOF in Example 1 has been removed by the adsorption over silica gel in this example, and therefore supporting that these colour forming compounds are polar compounds. The silica gel was washed by percolation with 20 ml of hexane, and the polar compounds were eluted by percolation with 10 ml of analytical grade ethanol.

Example 3

An amount of 32.8 grams of the commercial octenes B used in Example 1 were also percolated, as in Example 2, over 4.5 grams of silica gel. It was determined by similar spiking experiments as in Example 2, up to similar IV values, that no contributors to the Hot Sulphuric Acid Colour (Pt/Co scale) deterioration were remaining in the treated octenes.

Example 4

The polar materials that were adsorbed on the silica gel from the commercial octenes B in Example 3 were eluted by percolation from the silica gel with three times 5 ml of ethanol, after first washing the remaining olefins from the silica gel by a percolation treatment with five times 30 ml of heptane. A sample of the 15 ml (12 g) combined ethanol eluent mixture was subjected to ultra violet spectrophotometry and the spectrum showed a distinct absorption peak in the wavelength region of 225-230 nm, having a peak height of 0.4526. This UV spectrum is shown in FIG. 3. The absorption peak at about 190 nm is attributed to remaining olefins, however, the amount of olefins present in the sample was too weak to hide the peak at about 225 nm. Ethanol, into which about 0.08% of 2-methyl-2-pentenal was added as model compound for a conjugated unsaturated aldehyde, showed a strong and distinct absorption peak in exactly the same wavelength region. If one assumes the component absorbing in the specific wavelength region of 225-230 nm was 2-methyl-2-pentenal, the absorption peak height would convert pro-rata from the above external standard to a concentration of 0.367% wt in the ethanol eluent, or 0.134% wt in the octene feed. The latter corresponds to a concentration of 13.7 meq/kg of conjugated unsaturated aldehyde in the octenes.

Example 5

The ethanol eluent obtained from the extraction of polar compounds from the LOF in Example 2 was then mixed at different levels into the $C_9$ alcohol used in Example 1. The Hot Sulphuric Acid colours of the resulting mixtures were determined with the following results.

| Ethanol eluent added | Hot Sulphuric Acid Colour (Pt/Co scale) |
|---|---|
| 0.1% wt | 115 |
| 0.2% wt | 183 |
| 0.3% wt | 314 |

The ethanol eluents obtained from the extraction experiments in this example were subjected to GCMS using a polar GC column. Several components in the GCMS spectra were tentatively identified as unsaturated ketones or unsaturated aldehydes, and both spectra showed a significant number of peaks that could be attributed to such components.

Experiments 2 and 3 show that the potential contributors to the Hot Sulphuric Acid colour in the alcohol, present in the LOF byproduct from the alcohol and/or the olefin feed to the alcohol production process, can successfully be removed by adsorption on a polar adsorbent such as silica gel. Experiments 4 and 5 further show that these contributors may successfully be recovered from the silica gel by treatment with a polar solvent such as ethanol. The experiment also suggests that the potential contributors to the Hot Sulphuric Acid Colour reading may be unsaturated carbonyl compounds.

Example 6

Various amounts of 2-butenone, also called Methyl Vinyl Ketone (MVK) and being a compound which has conjugated unsaturation, and 5-hexene-2-one (here labelled 5Hx2O), an unsaturated ketone compound in which the unsaturation is not conjugated, were added to the $C_9$ alcohol as used in Example 1. The carbonyl concentrations and the Hot Sulphuric Acid Colours of the mixtures were measured with the following results.

| Addition | Carbonyl level (meq/kg) | Hot Sulphuric Acid Colour (Pt/Co scale) |
|---|---|---|
| 0.01% wt MVK | 2.3 | 121 |
| 0.02% wt MVK | 2.8 | 242 |
| 0.03% wt MVK | 4.2 | 328 |
| 0.01% wt 5Hx2O | 1.0 | 34 |
| 0.02% wt 5Hx2O | 2.0 | 45 |
| 0.03% wt 5Hx2O | 3.0 | 51 |

This example is showing that conjugated unsaturated carbonyl compounds are surprisingly much stronger potential contributors to the Hot Sulphuric Acid Colour than unconjugated unsaturated carbonyl materials. The impact of the unconjugated unsaturated carbonyl materials was found to be very similar to the effect of saturated carbonyl compounds, such as aldehydes, for the same carbonyl content, as demonstrated below.

Example 7

Figure 4:
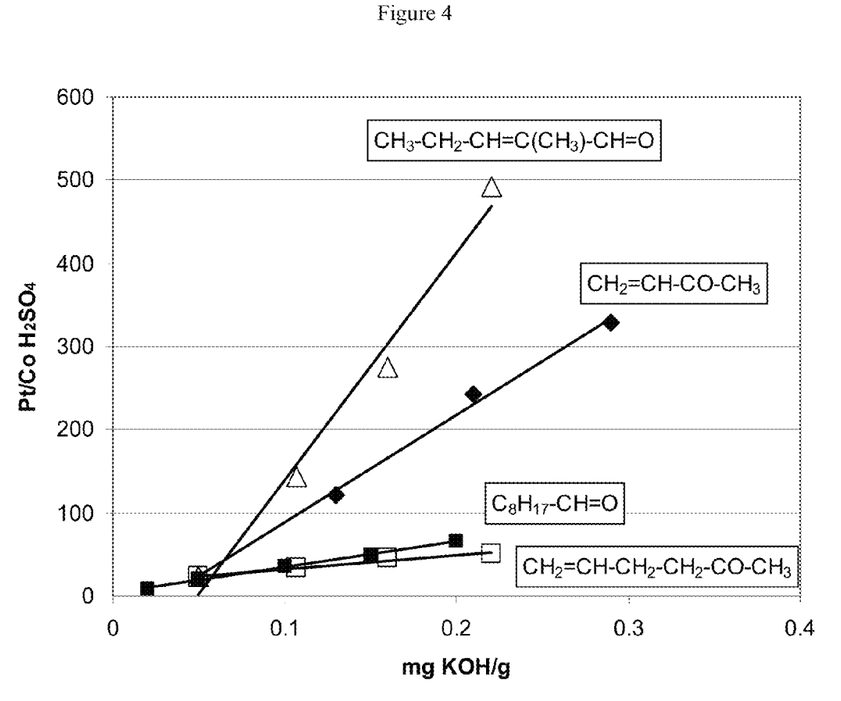
FIG. 4 is a graph showing the Pt/Co colour reading obtained when alcohols containing conjugated unsaturated carbonyl compounds, aldehydes or unconjugated unsaturated carbonyl compounds are subjected to the Hot Sulphuric Acid Colour test. The concentrations of the impurities in the abscissa are expressed as carbonyl number, with mg KOH/g as the units.

Various amounts of carbonyl containing compounds were added to a $C_9$ alcohol which had been distilled to a level that indicated zero carbonyl compounds and the products were subjected to the sulphuric acid colour test. The results are depicted in the graph that is FIG. 4, showing that the conjugated unsaturated aldehyde 2-methyl-2-pentenal has the most deleterious effect on colour formation, the conjugated unsaturated ketone MVK or 2-butenone is the next most deleterious, whereas the non-conjugated unsaturated ketone 5-hexen-2-one and the saturated $C_9$ aldehyde have considerably less effect on Hot Sulphuric Acid colour formation.

Example 8

In this example, the UV spectrophotometry technique is calibrated. Model compounds (2,4-dimethyl-2-heptenal, a conjugated unsaturated aldehyde, and 2,4-dimethylheptanol) were prepared by the method described in U.S. Pat. No. 6,090,986, the contents of which is incorporated herewith by reference. Samples having a range of compositions were prepared that contained various low level concentrations of 2,4-dimethyl-2-heptenal, a model conjugated unsaturated aldehyde, in a sample consisting essentially of 2,4-dimethylheptanol. The concentrations of the 2,4-dimethyl-2-heptenal were confirmed by gas-liquid chromatography (GLC). The known compositions were submitted to the UV spectrophotometer testing as described hereinbefore, whereby a cell was selected to give an absorbance reading in the range 0.15-2.0. The values of absorbance (A) measured at the absorption peak around 210-230 nm and divided by the path length p of the cell in cm, together with the wt ppm of 2,4-dimethyl-2-heptenal present in the compositions, also converted into milli-equivalents of conjugated unsaturated carbonyl compound per kg of composition, were as follows:

| C9-enal | | absorbance |
|---|---|---|
| wt ppm | meq/kg | A/p |
| 19.6 | 0.140 | 1.78448 |
| 17.1 | 0.122 | 1.71994 |
| 15.5 | 0.110 | 1.49158 |
| 14.1 | 0.100 | 1.38347 |
| 9.9 | 0.071 | 1.01111 |
| 11.5 | 0.082 | 1.15089 |
| 7.8 | 0.056 | 0.83333 |
| 3.1 | 0.022 | 0.39035 |
| 5.8 | 0.042 | 0.61938 |
| 4.6 | 0.033 | 0.52046 |
| 2.4 | 0.017 | 0.28793 |
| 1.8 | 0.013 | 0.18311 |

The measurements demonstrate a linear response of the measured A/p value with the concentration, over the entire range that was tested, such that a calibration curve may be developed and the UV measurement thus may be suitable for quantitative determination of the content of conjugated unsaturated carbonyl compounds in alcohol compositions. The data also demonstrate that the technique may readily be suitable for determining concentrations down to 0.02 meq/kg or below.

Having now fully described this invention, it will be appreciated by those skilled in the art that the invention can be performed within a wide range of parameters within what is claimed, without departing from the spirit and scope of the invention.

What is claimed is:

1. A $C_4$ to $C_{15}$ alcohol composition comprising at most 1.78 meq/kg of conjugated unsaturated carbonyl compounds, whereby,
   (i) if the nominal average carbon number of the alcohol mixture is 6, the mixture contains at most 0.99 meq/kg of conjugated unsaturated carbonyl compounds,
   (ii) if the nominal average carbon number of the alcohol mixture is 7 or 8, the mixture contains at most 0.17 meq/kg of conjugated unsaturated carbonyl compounds,
   (iii) if the nominal average carbon number of the alcohol mixture is 9 or 13, the mixture contains at most 0.88 meq/kg of conjugated unsaturated carbonyl compounds, and
   (iv) if the nominal average carbon number of the alcohol mixture is 10, the mixture contains at most 1.05 meq/kg of conjugated unsaturated carbonyl compounds.

2. The alcohol composition according to claim 1 having an average branchiness per molecule in the range of from 0.1 to 4.0.

3. The alcohol composition according to claim 1 wherein at most 90% by mole of the alcohol molecules have their first branch on the second carbon position relative to the OH-function.

4. An ester derived from an esterification reaction of the $C_4$ to $C_{15}$ alcohol according to claim 1 and an organic acid or anhydride, wherein the esterification reaction employs an organic metal compound catalyst.

5. The ester according to claim 4 which is an ester of the alcohol with an acid selected from the group consisting of benzoic acid, adipic acid, phthalic acid, isophthalic acid, terephthalic acid, trimellitic acid, cyclohexane monocarboxylic acid, cyclohexane 1,2, 1,3 or 1,4 dicarboxylic acid, and any of their anhydrides.

6. A composition comprising the ester according to claim 4 and polyvinyl chloride.

7. A synthetic lubricant comprising the ester according to claim 4.

* * * * *